United States Patent [19]

Sanvordeker et al.

[11] Patent Number: 5,047,244
[45] Date of Patent: Sep. 10, 1991

[54] MUCOADHESIVE CARRIER FOR DELIVERY OF THERAPEUTICAL AGENT

[75] Inventors: Dilip R. Sanvordeker, Irvine; Sau-Hung S. Leung, Corona, both of Calif.

[73] Assignee: Watson Laboratories, Inc., Corona, Calif.

[21] Appl. No.: 202,662

[22] Filed: Jun. 3, 1988

[51] Int. Cl.$^5$ .................... A61F 13/00; A61K 9/26
[52] U.S. Cl. .................... 424/435; 424/434; 424/443; 424/448; 424/484; 424/486; 424/78
[58] Field of Search .................... 424/434–435, 424/484–488, 448, 447, 434, 435

[56] References Cited

U.S. PATENT DOCUMENTS

| | | | |
|---|---|---|---|
| 3,551,556 | 12/1970 | Kliment et al. | 424/434 |
| 3,911,099 | 10/1975 | DeFoney et al. | 424/435 |
| 4,704,119 | 11/1987 | Shaw et al. | 424/448 |
| 4,740,365 | 4/1928 | Yukimatsu et al. | 424/435 |

FOREIGN PATENT DOCUMENTS

| | | | |
|---|---|---|---|
| 2497098 | 7/1982 | Japan | 424/435 |
| 0015829 | 1/1986 | Japan | 424/435 |

Primary Examiner—Thurman K. Page
Assistant Examiner—James M. Spear
Attorney, Agent, or Firm—Dressler, Goldsmith, Shore, Sutker & Milnamow, Ltd.

[57] ABSTRACT

A mucoadhesive carried suitable for a therapeutic agent is disclosed. This carrier allows controlled release of the therapeutic agent via mucosal tissue. The mucoadhesive carrier comprises a Monolithic polymer matrix that is anhydrous but hydratable, and amorphous fumed silica. The silica enhances the mucoadhesive properties of the carrier. An optional water-insoluble barrier film or layer can be secured to the polymer matrix to provide a non-adhering face.

11 Claims, 1 Drawing Sheet

MUCOADHESIVE CARRIER FOR DELIVERY OF THERAPEUTICAL AGENT

TECHNICAL FIELD

This invention relates to a carrier system for administration of a therapeutic agent via a mucosal membrane. In particular, the carrier system exhibits enhanced adhesion to the mucosal membrane and provides improved bioavailability of the therapeutic agent.

BACKGROUND OF THE INVENTION

Delivery of drugs by the buccal route of administration and therapeutic compositions and methods therefor have been described previously in U.S. Pat. Nos. 3,133,862 to Wershaw et al., 3,536,809 to Applezweig, 3,598,122 to Zaffaroni, 3,598,123 to Zaffaroni, 3,972,995 to Tsuk et al., 4,226,848 to Nagai et al., 4,250,163 to Nagai et al., 4,292,299 to Hicks et al. and 4,615,697 to Robinson. Robinson provides a review of delivery of drugs via mucosal routes and percutaneous routes. Buccal drug delivery systems with bioadhesive polymers as a platform for holding the system in place in the oral cavity after application have been described in the aforementioned U.S. Patents to Tsuk et al., to Nagai et al., to Hicks et al. and to Robinson. In most of these patents the drug is incorporated in a reservoir in the adhesive layer or embedded in the controlled release matrix without the use of any specific agent to promote drug dissolution and thereby enhance the thermodynamic activity of the drug in the matrix.

In U.S. Pat. No. 3,598,123 to Zaffaroni, a microcapsule encloses the drug as an added reservoir embedded in the adhesive layer of the bi-laminate drug delivery system.

Previously, a method of adhering a delivery system was by hydration of a bioadhesive polymer matrix. Adhesion results from the entanglement of the hydrated polymer chains on the surface of the matrix with the glycoproteins of the mucosa. Under mild pressure such entanglement leads to a reinforcement of adhesion due to London dispersion forces (e.g. van der Waal's forces), as well as hydrophobic, ionic and hydrogen bonding forces that contribute to the adhesion strength.

The inclusion of drugs as a dispersion in polyethylene glycols improves both the solubility and disolution rate and thereby improves the bioavailability of poorly water soluble drugs. Their uses in improving solubility and lowering the polarity of a solvent and dielectric constant of aqueous media are documented in Chiou et al., *J. Pharm. Sci.* 58, 1505 (1969), Ingham, *Arch. Biochem. Biophys.* 184, 59 (1977), Herrmann et al., *Biochim. Biophys. Acta* 733, 87 (1983), Arnold et al., *Biochim. Biophys. Acta* 815, 515 (1985). More specifically, it has been demonstrated previously that partitioning of hydrophobic as well as polar molecules between the membrane and external phase is changed by polyethylene glycols without interacting in a direct manner with macromolecules or other membrane components.

The carboxy-functional polymers disclosed in Robinson are hydratable polymers which are useful for buccal delivery of drugs. These polymers rely solely on the adhesion of the delivery system followed by drug dissolution in the hydrophilic polymer matrix due to a body fluid such as saliva or its aqueous component to effect release of the drug. In these systems, the chemical potential or the thermodynamic activity of the drug is built up to the point of saturation solubility of the drug in the micro-fluid environment of the polymer matrix. Consequently, the drug is released out of the matrix into the buccal interfacial environment at a rate dependent on the saturation solubility of the drug in the body fluid which permeates the matrix. Thus there is little control over the rate of release. Furthermore, for polar drugs, including zwitter-ionic therapeutic compounds such as bio-synthetic peptides which are subject to poor oral bioavailability, there is a lack of a relatively non-polar microfluid environment at the diffusional interface of the polymer matrix and the buccal mucosa. Thus, solubility of these drugs is poor.

The systems presently utilized therefore, are based solely on Fickian diffusion of the drugs through the polymer matrix. Diffusion rates are limited by the low chemical or thermodynamic activity and a highly polar aqueous environment. These limiting factors are detrimental to improved drug partitioning and permeability across the buccal mucosa.

It is recognized that many drugs are relatively insoluble and more lipophilic in their physical-chemical characteristics. Illustrative drugs in different therapeutic classes include estrogens, contraceptives, steroids, androgens, nifedipine, flufenamic acid and its analogs, spironolactone and griseofulvin. Hence improvement in thermodynamic activity of such drugs in a controlled release matrix combined with a favorable drug partitioning environment would facilitate mucosal drug delivery.

The present invention discloses methods and compositions that are capable of providing improved availability for a wide variety of therapeutic agents from a controlled release mucoadhesive carrier system thereby overcoming the shortcomings of the prior art and satisfying the present needs of society.

SUMMARY OF THE INVENTION

The present invention contemplates an anhydrous but hydratable mucoadhesive monolithic polymeric matrix which includes amorphous fumed silica present in an amount sufficient to enhance adhesion of the polymeric matrix to mucosal tissue. Optionally, the matrix may include a plasticized, film-forming cellulose ester.

This present polymeric matrix is mucoadhesive, and is eminently well suited for systemic delivery of a wide variety of therapeutic agents via the mucous membranes of a patient, i.e., by buccal, vaginal or rectal route. Therapeutic agents which exhibit absorption problems by the gastro-intestinal route due to solubility limitations, pH or enzymatic degradation and/or extensive metabolism by the liver are particularly well suited for use in combination with the present carrier. These agents can be hydrophilic, hydrophobic or amphiphilic in nature and can belong to a specific therapeutic class or within an area covering cardiovascular, bronchodilation, growth-stimulating supplements, enzyme supplements, estrogen and androgen supplements, anti-anxiety, antidepressant, anti-parkinsonism, memory maintenance, memory retention or enhancement, birth-control, antibiotic, antiviral, antiprotozoal, vitamin, antidiabetic, gastro-intestinal, anticonvulsant, immunomodulation, nutritional supplements and appetite modulating therapy.

DETAILED DISCLOSURE OF THE PREFERRED EMBODIMENTS

Figure 1:
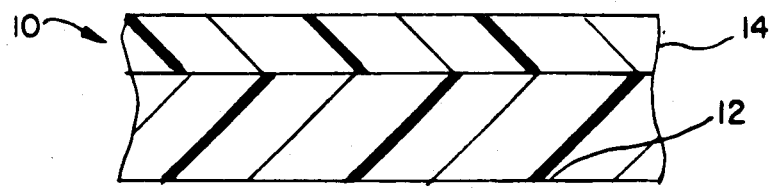
FIG. 1 is a fragmentary sectional view showing the bi-laminate structure of a mucoadhesive therapeutic dosage form embodying the present invention.

The term "mucoadhesive", as used herein, is a material that adheres to a mucosal tissue surface in-vivo and/or in-vitro. Such adhesion will adherently localize the dosage form onto the mucus membrane and requires the application of a force of at least about 50 dynes/cm$^2$ to separate the mucoadhesive material from the mucus membrane.

All mesh sizes are U.S. Sieve Series.

The mucoadhesive carrier of the present invention can be fabricated in a wide variety of self-supporting sizes, shapes or forms that provide a therapeutic dosage form suitable for comfortable and convenient application and adhesion to the buccal, vaginal or rectal mucosa. The mucoadhesive carrier can be fabricated in the form of a disc of a suitable size and shape, a hard or soft film, or an implantable form, for example. An optional water-insoluble barrier film can be provided on the mucoadhesive carrier so as to render a side or face thereof non-adhesive.

The present mucoadhesive carrier comprises a monolithic polymer matrix that is anhydrous but hydratable, and amorphous fumed silica present in an amount sufficient to enhance adhesion of the matrix to tissue as is more fully described hereinbelow. A therapeutic agent is distributed within the carrier as a solution or a dispersion therein.

Examples of therapeutic agents capable of being delivered by the foregoing carrier are 17 β-estradiol, dehydroepiandrosterone, nifedipine, diltiezem, haloperidol, buprenorphine, meperidine, fentanyl, testosterone, progesterone, norethindrone, ethinyl estradiol, mestranol, oxandrolone, and the like. Therapeutic agents which are relatively insoluble in water can be combined with a polyol such as a polyethylene glycol (PEG) which is then admixed with the amorphous fumed silica to form the matrix. Therapeutic agents which are amphiphilic and water soluble also can be admixed with the hydrophilic polyol to form a dispersion which is then combined with the silica.

Preferred polymers for the polymeric matrix are polyols, e.g., polyethylene glycols (PEG) having a number average molecular weight in the range of about 1500 to about 8500, preferably in the range of about 4000 to about 8000. These polyols promote lowering of the dielectric constant of the aqueous environment to which the carrier is exposed and solubilize relatively insoluble agents thereby increasing the thermodynamic activity of the therapeutic agent in the monolithic polymer matrix. Enhancement of the diffusion of the therapeutic agent across the matrix into the mucosa and the capillary bed of the mucosal tissue underneath is thus achieved. Additionally, these polyols have the distinct advantage of being inert, pharmaceutically acceptable adjuvants.

Furthermore, the mucoadhesive carrier composition can optionally include an additional amount of the same polyol or a derivative having a higher or lower number average molecular weight. The additional polyol is believed to function as a plasticizer and diffusion aid.

Hydrophilic polyols, which are water-soluble provide very favorable dissolution of the therapeutic agents. These hydrophilic polyols create a less polar aqueous environment by lowering the dielectric property of the aqueous solution of the mucosal environment. Thus, the hydrophilic polyols described herein are believed to function as a dissolution promoter and/or facilitator of therapeutic agent transport through the polymer matrix as well as interfacial transport across a biological membrane such as the mucosa.

The mucoadhesive carrier composition is combined with a therapeutic agent as a dispersion or solution of the therapeutic agent in a stable melt-processable form of the polymer, such as polyethylene glycol having a melting point of at least about 50° C. (about 120° F.). The composition is processable by melt, solvent deposition or physical blending processes.

Amorphous fumed silica is added to the polymeric matrix in a processable dry powder form. The amount of fumed silica present varies, depending on the nature of the polymeric matrix utilized in any given instance; however, the amount of fumed silica added is sufficient to enhance the adhesion of the polymeric matrix to mucosal tissue. If the polymeric matrix is constituted primarily by a polyol, the amount of fumed silica present preferably is at least about 10 percent by weight of the matrix. On the other hand, if the polymeric matrix also includes other known bioadhesives such as a carboxy-functional polymer, the amount of fumed silica present can be as low as about 2 percent by weight of the matrix, and preferably is at least about 3 percent by weight of the matrix. Examples of suitable silica are fumed silicon dioxide such as Cab-o-sil ® (Degussa Corp., Teterboro, N.J.), Aer-o-sil ® (Degussa Corp.) or microporous precipitated silicon dioxide such as Syloid ® (Davison Division, W. R. Grace Company) available commercially in food and pharmaceutical grades. The silica serves to provide a plurality of discrete particles that are distributed within and/or on the surface of the monolithic polymeric matrix of the present carrier.

Additionally, the silica can serve as a reservoir for a therapeutic agent.

While not willing to be limited to a specific function, it is presently believed that mucoadhesion occurs due to bulk convective capillary flow of the aqueous mucus-loaded fluid into the micro-environment of the microporous silica particles. These discrete particles serve as hydrating absorbent components and are believed to draw components or portions of the glycoprotein from the mucous of the mucosal wall into the microporous silica particles at the surface and/or in the polymer matrix, as the case may be. During hydration of these water-insoluble microporous silica particles, the entanglement of portions of mucoproteins from the mucosal wall occurs leading to a reinforced adhesion brought about by the naturally applied pressure of the mucosal wall which holds the drug delivery system in place.

An optional bioadhesive such as a water-swellable, but water-insoluble, fibrous, cross-linked carboxy-functional polymer can also be present. This polymer contains a plurality of repeating units of which at least about 80 percent contain at least one carboxyl functionality and about 0.05 to about 1.5 percent cross-linking agent substantially free from polyalkenyl polyether, with the percentages being based upon the weights of unpolymerized repeating unit and cross-linking agent, respectively. In more preferred practice, at least about 90 percent of the repeating units contain at least one carboxyl functionality, and in still more preferred practice, at least 95 percent of those repeating units contain at least one carboxyl functionality. Most preferably, the bioadhesive is a reaction product of the polymerization of only a carboxyl-functional monomer and a cross-linking agent therefor. Also in more preferred practice, the bioadhesive contains about 0.1 to about 1 percent by weight of polymerized cross-linking agent. Such a bioadhesive is commercially available under the trademark Carbophil® from B. F. Goodrich, Cincinnati, Ohio.

Other optional bioadhesives include polymers which are hydrophilic and water-dispersible, have free carboxylic groups and a relativey high base binding capacity. Preferred polymers include water dispersible polycarboxylated vinyl polymers. Polyacrylic acid polymers are particularly preferred. The average number molecular weight of this polymer is desirably in the range of about 1,250,000 to about 3,000,000. Suitable polyacrylic acid polymers include, but are not limited to, polyacrylic acid polymers lightly crosslinked with a polyalkenyl polyether such as those commercially available from B. F. Goodrich, Cincinnati, Ohio, under the trademarks Carbopol® Ex 55 Resin, 434, 934P, 940 and 941.

The cumulative mucoadhesive effect of these microporous silica particles on the carrier, with or without the inclusion of a known bioadhesive such as Carbopol®, Carbophil® and combinations thereof, has not been reported to the best of our knowledge.

In addition to the silica serving as a mucoadhesive, it can also serve as a reservoir for the controlled release of the therapeutic agents. Inclusion of a therapeutic agent loaded portion of silica powder serves as a reservoir for a variety of therapeutic agents or their derivatives with varying physical properties such as melting points, partition coefficient, crystal form and intrinsic dissolution rates.

The mucoadhesive carrier composition can also be combined with known natural or synthetic hydratable adjuvants or a mixture thereof, such as polyvinyl alcohol, polyvinyl pyrrolidone (povidone), sodium alginate, methyl cellulose, hydroxyl propyl cellulose, hydroxypropylmethyl cellulose, polyethylene glycols, carbopol, polycarbophil, carboxyvinyl copolymers, propylene glycol alginate, alginic acid, methyl methacrylate copolymers, (Eudragit® type, from Rohm Pharma, N.Y., N.Y.), tragacanth gum, guar gum, karaya gum, ethylene vinyl acetate, dimethylpolysiloxanes, polyoxyalkylene block copolymers (Poloxamers, the Cosmetic, Toiletry and Fragrance Association, Inc. name for a commercially available polyoxyethylene-polyoxypropylene block copolymer) hydroxyethylmethacrylate copolymers and the like to increase the tortuosity of the therapeutic agent-containing monolithic polymer matrix.

The dissolution of the therapeutic agent within the monolithic polymer matrix is enhanced by maintaining a high level of thermodynamic activity of the therapeutic agent. This activity is maintained by utilizing hydrophilic and hydrophobic excipients in combination, e.g., polycarbophil and glyceryl behenate, respectively, in the polymer matrix to control the release of the therapeutic agent for superior bioavailability.

The resulting monolithic polymer matrix can be optionally laminated to a water-insoluble, but water-permeable or substantially water-impermeable, barrier film which does not contain the therapeutic agent. The barrier film serves as a backing to prevent or minimize back diffusion of the therapeutic agent and protect the extraneous tissues, such as gums and teeth, from direct exposure to the matrix. The composition of the water-insoluble barrier film is chosen in such a manner as to be compatible with the polymer matrix and so that it is stable and non-irritating to the patient. Preferably, components of this barrier film include components of the polymer matrix to ensure compatibility, processability and physical stability of the carrier system during the shelf life of the product.

The barrier film may include pharmaceutically edible adjuvants. Illustrative adjuvants include hydrogenated vegetable oil, microcrystalline cellulose, methylcellulose, calcium phosphate dihydrate, talc, kaolin, bentonite, hydroxypropyl cellulose, high melting glyceryl esters such as glyceryl behenate, methylcellulose, cellulose acetate butyrate, polyvinyl pyrrolidone, polyvinyl alcohol, magnesium stearate, silicon dioxide, and stearic acid.

Preferably, major components of the barrier layer or film are directly compressible, water-insoluble materials such as dicalcium phosphate dihydrate (Encompress®, Edward Mendell Co. Inc., Carmel, N.Y.) and glyceryl behenate (Compritol®, Gattefosse Corporation, Elmsford, N.Y.) together with a minor amount of a cellulose derivative. Inclusion of these ingredients improves cost-effective manufacture of a bi-laminate tablet or disc type dosage form that can be blister packed or foil packed for convenient dispensing by the patient. Furthermore, the use of a hydrophilic, water-insoluble inorganic excipient such as dicalcium phosphate dihydrate in combination with a hydrophilic agent provides a satisfactory drug permeation barrier, for bi-laminate carriers for mucosal applications.

A preferred embodiment of the present carrier is a mucoadhesive disc composed of a bi-laminate including a water-swellable, hydratable monolithic polymer matrix and a water-insoluble barrier film. The mucoadhesive polymer matrix contains a dispersion of the therapeutic agent in an amount sufficient for the desired medical treatment.

The following is an illustration of a composition and a process for manufacturing the present invention.

The polymer matrix is provided by a polyol in which is dispersed amorphous fumed silica and the desired medicament. The hydrophilic polyol is preferably, a polyethylene glycol (PEG), more preferably a melt-processable powder form of PEG having a melting point of at least about 50° C. (about 120° F.). The number average molecular weight of the PEG is in the range of about 1500 to about 8500, preferably about 4000 to about 8000. The weight ratio of the therapeutic agent: hydrophilic polyol is in the range of about 500:1 to about 0.1:500, preferably about 1:2 to about 1:5, respectively.

Silica having a microporous structure and a surface area in the range of about 300 m$^2$/g to about 700 m$^2$/g is present in an amount of about 0.1 to about 40, preferably about 10 to about 35 weight percent, based on the total weight of the polymeric matrix including the weight of the silica.

The silica utilized in the resulting mucoadhesive composition can be utilized alone or in combination with optional components such as a known hydratable, bioadhesive polymer, e.g., polycarbophil, or a diffusion retarding polymer such as a polyvinyl alcohol or a high viscosity grade hydroxypropyl cellulose (Klucel ® HXF, Hercules, Inc., Houston, Tex.). These optional components can be present in the range of up to about 50 weight percent, based on the total weight of the polymer matrix.

To maintain a high level of thermodynamic activity of the therapeutic agent a preferred combination of a hydrophobic excipient with a hydrophilic excipient present in the monolithic polymer matrix is glyceryl behenate (Compritol ®, Gattefosse Corp., Elmsford, N.Y.) and polycarbophil, respectively. The weight ratio of hydrophobic to hydrophilic excipient is in the range of about 1:20 to about 3:1, preferably about 1:10 to about 1:1. Up to about 50 weight percent, based on the total weight of the polymer matrix, of this combination can be present.

Other relatively water-insoluble but hydratable adjuvants that increase the tortuosity of the polymer matrix are dicalcium phosphate dihydrate (Encompress ®), fully hydrolyzed polyvinyl alcohol (Vinol ® 125, Air Products and Chemicals Inc., Allentown, Pa.) and dry microporous and microfine silicon dioxide. A preferred range of the total amount of these polymer matrix forming adjuvants is about 0.5 to about 50 weight percent based on the total weight of the polymer matrix.

The components of the polymer matrix can be blended and lubricated, if necessary, with known lubricants such as magnesium stearate, sodium fumarate, stearic acid or talc, optionally present in the range of about 0.5 to about 2 weight percent based on the total weight of the polymer matrix.

The barrier film, as an optional but preferred element of this invention, is composed of a combination of pharmaceutical excipients similar to those that are used in the polymer matrix and more importantly, that are relatively water-insoluble and in a laminate form provide a non-disintegrating therapeutic agent-impervious barrier film or layer to inhibit back diffusion of the therapeutic agent from the polymer matrix.

Preferred ingredients useful but not exclusive to the compositions of the barrier film are dicalcium phosphate dihydrate (Encompress ®) in the range of about 10 to about 25 weight percent and a colorant, preferably an aluminum lake, such as FD&C red #40 lake (from Coloron, Inc.) in the range of about 0.1 to about 1 weight percent. Hydrophilic polymers such as fully hydrolyzed polyvinyl alcohol (Vinol ® 125) of a fine grade (40 mesh, U.S. Sieve Series) in the range of about 1.0 to about 50.0 weight percent and a high viscosity grade hydroxypropyl cellulose (Klucel ® HXF) in the range of about 3 to about 20 weight percent which function as moisturizers or binders thereby maintaining the integrity of the laminate are also suitable for use in the barrier film. All weight percents are based on the total weight of the barrier film.

The polymeric matrix and the barrier film usually are prepared separately. The following are illustrative methods of preparing the polymeric matrix.

An illustrative melt process produces a mucosal composition in which the therapeutic agent is dissolved in the polyethylene glycol. In this process, the polyethylene glycol is melted, usually at a temperature of about 70° C. (about 160° F.). The powdered therapeutic agent is then slowly added to the molten polyethylene glycol under constant stirring. Stirring is continued until all the therapeutic agent particles present are dissolved. The thus produced liquid mucosal composition is then poured onto a surface, i.e., flattened aluminum foil, and solidified. Additional cooling, if desired or necessary to provide a relatively rapid solidification, can be performed by placing the composition in an airtight container which is placed in a freezer at a temperature of about 4° C. (about 40° F.).

Alternatively, in an illustrative dry blend process, the powdered polyethylene glycol and therapeutic agent are intimately admixed to produce the desired physical admixture.

The above mucosal composition or physical admixture is then finely ground to a powder of about 60 to about 80 mesh and blended with other matrix forming hydrophilic and hydrophobic excipients of the polymer matrix such as glyceryl behenate (Compritol ®), polyvinyl alcohol, dicalcium phosphate dihydrate (Encompress ®), hydroxypropyl cellulose (Klucel ® HXF) and silica in the form of microporous, microfine silicon dioxide (Sylloid ® 224 FP, Davison Division, W. R. Grace & Company). Optionally, additional polyethylene glycol can be added. A granulation process utilizing an organic solvent or water may be used to prepare, dry and obtain granules in a range of about 40 to about 200 mesh. This resulting dried preparation of the polymer matrix can optionally be blended and lubricated with the aforementioned lubricants.

In a similar manner the barrier film or layer is prepared separately utilizing some of the constituents of the polymer matrix with the exception that the barrier film or layer does not contain a therapeutic agent or an adhesive.

The components of the polymer matrix and the barrier film in their required portions are compressed together as by a hydraulic press, e.g., a Carver Press, to obtain a bi-laminate mucoadhesive carrier of a suitable size and shape.

A preferred range for the thickness of the mucosal composition containing monolithic polymer matrix is about 0.5 mm to about 10 mm. A preferred range for the thickness of the barrier film is about 0.5 mm to about 20 mm. These sizes are dependent upon the requirements of the dose, site of application and delivery rate of the therapeutic agent for an effective therapy via application of the system on the mucosal site for a specified period.

A preferred shape for the delivery system depends on the site of application. It can be a flat disc, rectangular, circular, oval, oblong, rod, bi-convex or hemispheric shaped. A preferable shape of the carrier is a disc shape 5 mm to 50 mm in diameter.

Optionally a retrieving element which is an appendage extending from the carrier is present to facilitate removal.

The carrier of the present invention may have various configurations. Illustrative configurations are shown in FIGS. 1-5.

FIG. 1 shows therapeutic dosage form 10 of the present invention comprised of a mucoadhesive polymer matrix 12 containing a dissolved therapeutic agent and having attached thereto optional barrier film or layer 14 which provides a non-adhesive face.

Figure 2:
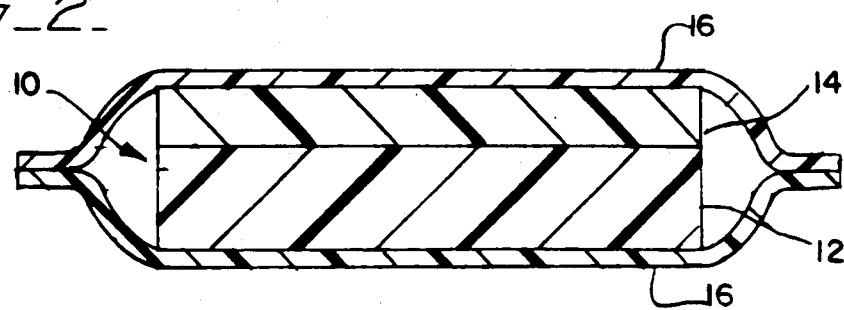
FIG. 2 is a sectional view showing the dosage form of FIG. 1 enclosed within a protective envelope.

In FIG. 2, the dosage form 10 is enclosed in a protective envelope 16 which protects the dosage form 10 from the external environment prior to use. This protective envelope 16 is substantially water vapor impermeable and is composed of an appropriate packaging material such as aluminum foil or the like.

Figure 3:
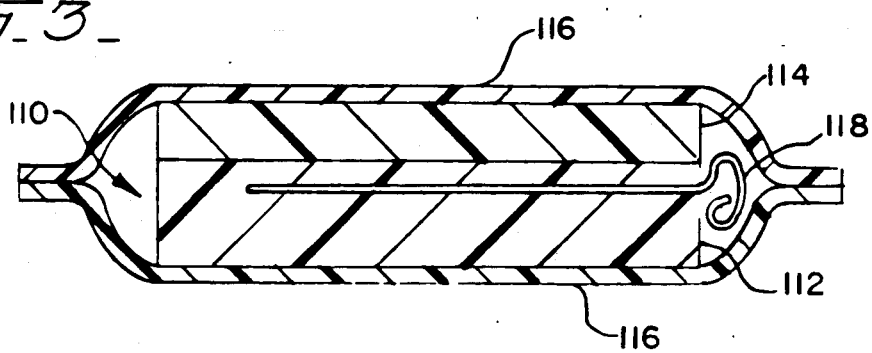
FIG. 3 is a sectional view of an alternative embodiment of the present therapeutic dosage form having a retrieving element therein.

FIG. 3 shows an alternative embodiment of therapeutic dosage form 110 enclosed in the protective envelope 116. In this alternative embodiment, a retrieving element in the form of a string-like segment 118 is present. The function of the retrieving element is to assist in removal of the dosage form 110 from the user. While FIG. 3 shows the string-like segment 118 embedded within the polymer matrix 112, the location of the segment 118 is not critical so long as the segment 118 can be conveniently grasped and manipulated to perform its intended function.

Figure 4:
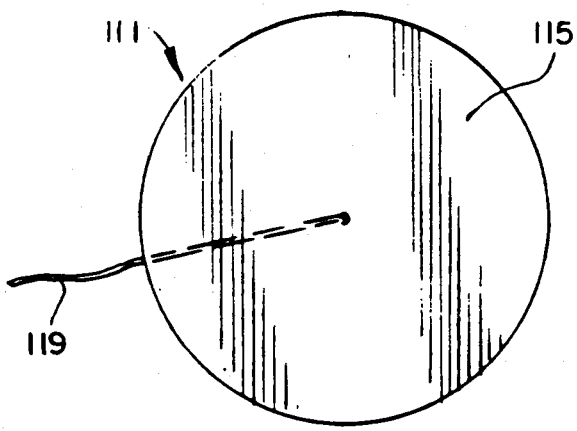
FIG. 4 is a planar view of an alternative embodiment of the present therapeutic dosage form also provided with a retrieving element.

FIG. 4 is a planar view of a mucoadhesive spherical dosage form 111 showing the retrieving element 119 anchored within the polymeric matrix 115.

Figure 5:
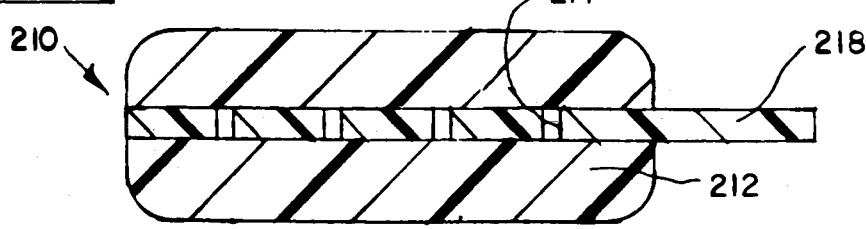
FIG. 5 is a sectional view of yet another embodiment of the present therapeutic dosage form showing an alternative retrieving element provided with perforations.

Yet another embodiment of a mucoadhesive dosage form is shown in FIG. 5. In this embodiment, dosage form 210 is provided with embedded planar retrieving element 218 in the form of a ribbon which is provided with perforations 214 that facilitate the anchoring of the retrieving element 218 within the polymeric matrix 212.

Various tests were conducted showing the effectiveness of the present invention. These tests are described hereinbelow.

EXAMPLE 1

Preparation of bioadhesive discs which do not embody the present invention

For each layer, all the individual ingredients, disclosed in TABLE I, below, were weighed accurately and mixed in an opaque bottle for about two minutes. Each mixture was then passed through a 45 mesh screen three times. The screened mixture was collected in a bottle and mixed for an additional 2 minutes. Approximately 130 mg of the composition of the barrier layer was weighed and placed in a circular stainless steel die having a 12.5 mm diameter and a flat stainless steel holder plug at the bottom. The powder was gently tapped to cover the die hole. Then 150 mg of the composition of the bioadhesive layer was added on the top of the barrier layer in the die. After an additional gentle tapping, the die and plate assembly was placed on a hand press with a fitting punch. Thin, approximately 12.5 mm×2.0 mm, bi-laminate circular discs weighing approximately 280 mg were pressed and recovered for in vivo bioadhesion testing in three female subjects as disclosed in EXAMPLE 2.

TABLE I

| Component | Bioadhesive layer Weight, (g) | Bioadhesive layer Weight percent | Barrier layer Weight, (g) | Barrier layer Weight percent |
|---|---|---|---|---|
| Dicalcium phosphate dihydrate[1] | 1.10 | 18.18 | 3.00 | 54.15 |
| Glyceryl behenate[2] | 0.22 | 3.64 | 2.00 | 36.10 |
| Colorant[3] | — | — | 0.04 | 0.72 |
| Magnesium stearate | — | — | 0.04 | 0.72 |
| Polyvinyl alcohol[4] | 0.28 | 4.63 | — | — |
| Hydroxypropyl cellulose[5] | 2.80 | 46.28 | 0.46 | 8.30 |
| Polycarbophil[6] | 1.65 | 27.27 | — | — |
| Total | 6.05 | 100.00 | 5.54 | 99.99 |

[1]Encompress ® from Edward Mendell Co. Inc., Carmel, NY, a commercially available dicalcium phosphate dihydrate.
[2]Compritol ® 885 from Gattefosse Corporation, Elmsford, NY, a commercially available glyceryl behenate.
[3]FD & C red #40 lake from Coloron, Inc., a commercially available aluminum lake colorant.
[4]Vinol ® 125 from Air Products and Chemicals, Inc., Allentown, PA, a commercially available polyvinyl alcohol.
[5]Klucel ® HXF from Hercules, Inc., Houston, Texas, a commercially available hydroxypropyl cellulose.
[6]Carbopol ® Ex-55 Resin from B.F. Goodrich Corp., a commercially available polycarbophil.

EXAMPLE 2

In vivo bioadhesion experiment

An in vivo bioadhesion experiment was performed using discs prepared in EXAMPLE 1. Three female subjects were chosen. Each subject placed the disc either on the upper right or upper left lip side of the buccal wall. The instructions were specific to ensure application of the non-colored side to the buccal wall. The subjects applied the discs after dinner and carried on with their normal activities such as brushing teeth and eating breakfast. After 12 hours, the subjects removed the discs and examined the condition of the disc after removal. Two subjects observed strong adhesion of the disc during the entire period of application. One subject experienced some difficulty in retaining it in place. The discs softened while in place, but remained intact during the entire period of application. After an initial period of about ½ hour, all subjects expressed a high level of product acceptance. There was no evidence of separation of the two layers.

EXAMPLE 3

Preparation of the mucoadhesive carrier of the present invention and hydration comparison of same with a bioadhesive disc The procedure for the preparation of discs was similar to that of EXAMPLE 1. The composition of the carrier is disclosed in TABLE II, below. For preparation of the discs, 150 mg each of the compositions of the polymer matrix and the barrier film were utilized. Additionally, bioadhesive discs without silicon dioxide were prepared. For the composition of the bioadhesive discs, the silica of the polymer matrix was replaced with hydroxypropyl cellulose. Both compositions with (I) and without (II) silica were compressed at 1000 psi and 10,000 psi compression pressure using a Carver Press. Samples of the mucoadhesive carrier and the bioadhesive disc, with and without silica, respectively, were tested for the rate and extent of hydration.

Samples, in triplicate, were weighed and placed in individual petri dishes filled with 0.1M, pH 7.0, phosphate buffer. At different time points, the buffer solution was drained and the petri dish blotted gently and carefully with micro-wipe paper to remove excess buffer solution without touching the sample. The sample was weighed to determine the increase in weight.

The rate and extent of hydration of the samples was studied for a time period up to 24 hours. TABLE III, below, presents the results of the hydration study. These results clearly demonstrate that aqueous penetration through the polymer matrix is rapid and that there is no statistically significant effect of compaction pressure on the rate or extent of hydration for the compositions tested.

TABLE II

| | Mucoadhesive Carrier Composition | | | |
|---|---|---|---|---|
| | Polymer matrix | | Barrier film | |
| Component | Weight, (g) | Weight percent | Weight, (g) | Weight percent |
| Dicalcium phosphate dihydrate[1] | 1.10 | 18.33 | 3.62 | 60.33 |
| Glyceryl behenate[2] | 0.22 | 3.67 | 2.00 | 33.33 |
| Colorant[3] | — | — | 0.04 | 0.67 |
| Magnesium stearate | — | — | 0.04 | 0.67 |
| Polyvinyl alcohol[4] | 0.30 | 5.00 | — | — |
| Hydroxypropyl cellulose[5] | 2.38 | 39.67 | 0.30 | 5.00 |
| Polycarbophil[6] | 1.80 | 30.00 | — | — |
| Fumed silica[7] | 0.20 | 3.33 | — | — |
| Total | 6.00 | 100.00 | 6.00 | 100.00 |

[1]Encompress ® from Edward Mendell Co. Inc., Carmel, NY, a commercially available dicalcium phosphate dihydrate.
[2]Compritol ® 885 from Gattefosse Corporation, Elmsford, NY, a commercially available glyceryl behenate.
[3]FD & C red #40 lake from Coloron, Inc., a commercially available aluminum lake colorant.
[4]Vinol ® 125 from Air Products and Chemicals, Inc., Allentown, PA, a commercially available polyvinyl alcohol.
[5]Klucel ® HXF from Hercules, Inc., Houston, Texas, a commercially available hydroxypropyl cellulose.
[6]Carbopol ® Ex-55 Resin from B.F. Goodrich Corp., a commercially available polycarbophil.
[7]Sylloid ® 244 FP from Davison Division of W. R. Grace and Company, a commercially available fumed silicon dioxide.

TABLE III

| | Mean (±S.D) Weight Percent Uptake of Buffer by Mucoadhesive Disc Compositions | | | |
|---|---|---|---|---|
| | Composition I[1] | | Composition II[2] | |
| Time (hr) | 1,000 p.s.i. | 10,000 p.s.i. | 1,000 p.s.i. | 10,000 p.s.i. |
| 0.75 | 98.71 ± 4.49 | 105.43 ± 15.28 | 114.87 ± 9.55 | 109.70 ± 14.89 |
| 2.00 | 159.52 ± 7.55 | 170.80 ± 6.59 | 193.58 ± 24.44 | 177.79 ± 32.37 |
| 4.00 | 233.70 ± 15.20 | 244.70 ± 17.16 | 290.92 + 41.49 | 265.68 ± 39.33 |
| 20.00 | 524.78 + 53.47 | 552.21 ± 68.85 | 628.00 ± 108.63 | 628.84 ± 129.65 |
| 24.00 | 594.38 ± 23.91 | 569.77 ± 49.01 | 738.14 ± 151.25 | 692.60 ± 92.26 |

[1]Mucoadhesive carrier with microporous silicon dioxide.
[2]Mucoadhesive carrier without microporous silicon dioxide.

EXAMPLE 4

In vivo mucoadhesion experiment

The composition of a mucoadhesive carrier in disc form using microfine and microporous silica as a mucoadhesive as disclosed in TABLE IV, below, was prepared and tested for in vivo adhesion in three female subjects.

TABLE IV

| Mucoadhesive carrier composition | | |
|---|---|---|
| Component | Polymer matrix Weight, (mg) | Barrier film Weight, (mg) |
| Dicalcium phosphate dihydrate[1] | 27.5 | 90.5 |
| Glyceryl behenate[2] | 5.5 | 50.0 |
| Colorant[3] | — | 1.0 |
| Magnesium stearate | — | 1.0 |

TABLE IV-continued

| Mucoadhesive carrier composition | | |
|---|---|---|
| Component | Polymer matrix Weight, (mg) | Barrier film Weight, (mg) |
| Polyvinyl alcohol[4] | 7.0 | — |
| Hydroxypropyl cellulose[5] | 60.0 | 0.75 |
| Fumed silica | 50.0 | — |

[1]Encompress ® from Edward Mendell Co. Inc., Carmel, NY, a commercially available dicalcium phosphate dihydrate.
[2]Compritol ® 885 from Gattefosse Corporation, Elmsford, NY, a commercially available glyceryl behenate.
[3]FD & C red #40 lake from Coloron, Inc., a commercially available aluminum lake colorant.
[4]Vinol ® 125 from Air Products and Chemicals, Inc., Allentown, PA, a commercially available polyvinyl alcohol.
[5]Klucel ® HXF from Hercules, Inc., Houston, Texas, a commercially available hydroxypropyl cellulose.
[6]Carpobol ® Ex-55 Resin from B.F. Goodrich Corp., a commercially available polycarbophil.

The procedure for preparation of the sample disc was similar to the one described in EXAMPLE 1. Two discs were dispensed to each subject for in vivo evaluation as described in EXAMPLE 2. Adhesion, integrity of the disc after removal, comfort during the application period and level of product acceptance was recorded by the subjects. The results are presented in TABLE V, below.

TABLE V

| | In vivo mucoadhesion evaluation | | | |
|---|---|---|---|---|
| | Test Parameter | | | |
| Subject | Adhesion | Integrity | Comfort | Product Acceptance |
| 1 | Excellent | Firm, Intact | Yes | High |
| 2 | Good | Intact | Tolerable | Low (disc too large) |
| 3 | Excellent | Intact | Yes | High |

The above test results demonstrate that dry, microporous and microfine silicon dioxide dispersed onto and within the matrix of a mucoadhesive carrier has the capability to mechanically hold on to the mucin of the buccal wall. None of the subjects had difficulty performing morning routines, such as brushing teeth and eating breakfast. The disc was observed to remain at the site for a period of 12 hours.

EXAMPLE 5

Preparation of a mucosal composition

Anhydrous mucosal compositions comprising one of the following therapeutic agents: nifedipine; estradiol; piroxicam; albuterol or dehydroepiandrosterone (DHEA), dissolved in polyethylene glycol were prepared. Each mucosal composition contained 0.5 grams of a therapeutic agent and 2.0 grams of polyethylene glycol 4000 which has a number average molecular weight of about 3350 (PEG 3350). Thus the weight ratio of therapeutic agent to PEG 3350 was 1:4, respectively. The mucosal composition was prepared by melting the weighed amount of PEG 3350 in a suitable vessel at about 70° C. (about 160° F.) on a hot plate. The powdered therapeutic agent was added slowly to the liquid PEG 3350 under constant stirring. The stirring of each molten mucosal composition was continued until all the therapeutic agent particles present dissolved.

The mucosal composition was then poured onto a flattened aluminum foil and allowed to solidify. Additional cooling of the mucosal composition containing the therapeutic agent and PEG 3350 was performed by placing the mucosal composition in an airtight container which was placed in a freezer at a temperature of about 4° C. (about 40° F.) for about one hour. The produced hardened flakes were powdered with a mortar and pestle and passed through a 60 mesh screen. The mucosal composition in powder form was then used for preparation of mucoadhesive carriers in disc form.

EXAMPLE 6

In vitro therapeutic agent release

In vitro therapeutic agent release studies were performed comparing a mucosal composition containing a therapeutic agent dissolved in PEG with a physical admixture of the same therapeutic agent with PEG. Approximately 450 mg of the mucosal composition containing piroxicam in an amount equivalent to approximately 90.0 mg of piroxicam (as prepared in EXAMPLE 5) and 450 mg of lactose, USP, were mixed intimately and compressed on a hand press into three circular discs for dissolution testing. Each circular disc weighed 300 mg and, each was 12.5 mm×2 mm in dimension.

A physical admixture was also prepared. 60 Mesh powders of piroxicam and PEG 3350 were intimately admixed in a 1:4 weight ratio. Approximately 450 mg of this admixture was blended with 450 mg of lactose, USP, to obtain the physical dispersion. Three circular discs each being of the above weight and dimensions were hand pressed for dissolution testing.

Therapeutic agent release studies were conducted using an Erweka dissolution test assembly in compliance with Dissolution Test Method II as described in The United States Pharmacopeia, 24th revision (USP XXIV). Five hundred milliliters of a 0.1M phosphate buffer dissolution fluid was maintained at about 37° C. (about 100° F.) and the basket was rotated at 50 revolutions per minute (rpm). At predetermined time points, samples of approximately 3 milliliters of the test medium were withdrawn from the flasks and immediately replaced with an equivalent volume of blank buffer. Analysis of the samples was performed by ultraviolet spectrophotometry. TABLE VI, below, illustrates dissolution performance of the mucosal composition and physical admixture of piroxicam. The time to achieve 20%, 50% and 80% by weight dissolution of the piroxicam was estimated from a linear plot of percent dissolved versus time.

TABLE VI

| | Piroxicam Release Parameter, (T[1]). | | |
|---|---|---|---|
| Dissolution test parameter time for piroxicam in a mucosal composition versus a physical dispersion under non-sink conditions | | | |
| Type | 20% | 50% | 80% |
| Mucosal composition | 7 | 21 | 30 |

TABLE VI-continued

| | Piroxicam Release Parameter, (T[1]). | | |
|---|---|---|---|
| Dissolution test parameter time for piroxicam in a mucosal composition versus a physical dispersion under non-sink conditions | | | |
| Type | 20% | 50% | 80% |
| Physical admixture | 18 | 44 | 60 |

[1]T is the time (in minutes) to achieve the depicted percent release of piroxicam.

As can be seen from the TABLE VI, there was a two fold decrease in time required for releasing an equivalent amount of piroxicam from the mucosal composition as compared to a physical admixture. The saturation solubility of piroxicam in 0.1M phosphate buffer was determined to be approximately 7.7 mg/ml. Even though sink conditions for dissolution testing were not maintained, this data clearly demonstrates that initial dissolution rate of piroxicam was by far greater for the mucosal composition than the physical admixture. Hence, development of a higher concentration gradient is to be expected after application of a mucosal carrier of the present invention. Controlled delivery of piroxicam is thus obtained.

EXAMPLE 7

In vitro therapeutic agent release

The compositions of TABLE VII, below, were utilized to prepare carriers. Each carrier contained 20 mg equivalent of one of the therapeutic agents, albuterol or norephedrine (phenylpropanolamine), in a mucosal composition having a therapeutic agent:polyethylene glycol 8000 (peg 8000) weight ratio of a 1:2, respectively. The mucosal compositions were prepared in accordance with the general procedure described in accordance with the general procedure described in EXAMPLE 5. 150 Mg each of the compositions of the polymer matrix and the barrier film were weighed and the mucoadhesive carriers in disc form were compressed at 1000 psi using a Carver Press following the general procedure described in EXAMPLE 1.

TABLE VII

Test Compositions for Albuterol and Phenylpropanolamine

| Component | Polymer matrix Weight, (mg) | Barrier film Weight, (mg) |
|---|---|---|
| Dicalcium phosphate dihydrate[1] | 27.5 | 90.50 |
| Glyceryl behenate[2] | 5.5 | 50.00 |
| Colorant[3] | — | 1.00 |
| Magnesium stearate | — | 1.00 |
| Polyvinyl alcohol[4] | 7.0 | — |
| Hydroxypropyl cellulose[5] | — | 0.75 |
| Polycarbophil[6] | 45.0 | — |
| Fumed silica[7] | 5.0 | — |
| Mucosal composition[8] | 60.0 | — |

[1]Encompress ® from Edward Mendell Co. Inc., Carmel, NY, a commercially available dicalcium phosphate dihydrate.
[2]Compritol ® 885 from Gattefosse Corporation, Elmsford, NY, a commercially available glyceryl behenate.
[3]FD & C red #40 lake from Coloron, Inc., a commercially available aluminum lake colorant.
[4]Vinol ® 125 from Air Products and Chemicals, Inc., Allentown, PA, a commercially available polyvinyl alcohol.
[5]Klucel ® HXF from Hercules, Inc., Houston, Texas, a commercially available hydroxypropyl cellulose.
[6]Carbopol ® Ex-55 Resin from B.F. Goodrich Corp., a commercially available polycarbophil.
[7]Sylloid ® 244 FP from the Davison Division of W. R. Grace and Company, a cmmercially available fumed silicon dioxide.
[8]Albuterol:PEG 8000 or Phenylpropanolamine:PEG 8000 weight ratio of 1:2.

Therapeutic agent release testing was conducted by the USP Dissolution Test Method II. The dissolution medium chosen was 500 ml of a 0.05M isotonic phosphate buffer having a 6.0 pH with 30 weight percent PEG 400. This method is described in EXAMPLE 6.

The results of therapeutic agent release studies of each individual composition are illustrated in TABLE VIII.

TABLE VIII

| Therapeutic Agent | Therapeutic Agent Release Parameter, (T[1]) | | | |
|---|---|---|---|---|
| | 20% | 50% | 75% | 90% |
| Albuterol | 0.58 | 3.16 | 5.67 | 6.83 |
| Phenylpropanolamine | 0.58 | 2.83 | 6.04 | 8.42 |

[1] T is the time (in hours) to achieve the depicted percent release of the therapeutic agent from the mucoadhesive carrier.

The results illustrated in TABLE VIII demonstrate therapeutic agent release from these compositions is controlled by the matrix composed of a combination of both hydrophilic and hydrophobic components that form the bilaminate structure of the mucoadhesive carrier.

EXAMPLE 8

Determination of the effect of hydrophilic and hydrophobic components on the release of the therapeutic agent from the polymer matrix.

Several compositions of mucoadhesive carriers containing albuterol were prepared to determine the effect of key hydrophilic and hydrophobic components of the monolithic polymer matrix on the release of albuterol from the polymer matrix. The compositions of these matrices are illustrated in TABLE IX, below. The methods of preparation of the mucosal composition as well as preparation of the carrier in disc form are substantially the same as those described in EXAMPLE 5 and EXAMPLE 6, respectively, except that the carrier included fumed silica as well.

The composition of the barrier film of this mucoadhesive therapeutic agent carrier was the same as that of the barrier film of EXAMPLE 4.

ter T (in hours) for a given weight and percent drug released was calculated from the plots. TABLE X, below, illustrates results of these studies. It can be concluded from these results that both an hydrophilic excipient such as polyvinyl alcohol or polycarbophil and an hydrophobic excipient such as glyceryl behenate retard albuterol release from the monolithic polymer matrix.

The ranges for these excipients can vary from virtually none, e.g., about 0.01 weight percent, to about 50 weight percent, to produce a desired therapeutic agent release profile.

TABLE X

| Composition | Therapeutic Agent Release Parameter, T[1] | | | |
|---|---|---|---|---|
| | 20% | 50% | 75% | 90% |
| a | 1.25 | 4.33 | 8.58 | 13.60 |
| b | 1.25 | 5.42 | 10.75 | — |
| c | 1.08 | 4.50 | 10.42 | — |
| d | 2.67 | 11.67 | — | — |
| e | 1.33 | 5.42 | — | — |
| f | 2.25 | 11.67 | — | — |
| g | 1.50 | 6.25 | — | — |
| h | 2.10 | 8.67 | — | — |
| i | 1.10 | 4.60 | — | — |
| j | 1.50 | 8.00 | — | — |

[1] T is the time (in hours) to achieve the depicted percent release of the therapeutic agent from the mucoadhesive carrier.

EXAMPLE 9

In vitro piroxicam release

The composition of TABLE XI, below, of a bi-laminate mucoadhesive carrier in disc form with 20 mg of piroxicam was prepared and tested for in vitro therapeutic agent release by the methods described previously in EXAMPLE 7.

TABLE XI

| Mucoadhesive carrier composition | | |
|---|---|---|
| | Weight, (mg) Per Carrier | |
| Component | Polymer matrix | Barrier film |
| Dicalcium phosphate dihydrate[1] | 27.50 | 90.50 |
| Glyceryl behenate[2] | 0.01 | 50.00 |

TABLE IX

| Component | Polymer Matrix Compositions Weight (mg) per carrier | | | | | | | | | |
|---|---|---|---|---|---|---|---|---|---|---|
| | a | b | c | d | e | f | g | h | i | j |
| Dicalcium phosphate dihydrate[1] | 0.01 | 122.50 | 27.50 | 27.50 | 27.50 | 27.50 | 27.50 | 27.50 | 27.50 | 27.50 |
| Glyceryl behenate[2] | 5.50 | 5.50 | 0.01 | 144.50 | 5.50 | 5.50 | 5.50 | 5.50 | 5.50 | 5.50 |
| Polyvinyl alcohol[3] | 7.00 | 7.00 | 7.00 | 7.00 | 7.00 | 7.70 | 7.70 | 7.70 | 0.01 | 143.00 |
| Hydroxypropyl cellulose[4] | — | — | — | — | 0.01 | 150.00 | — | — | — | — |
| Polycarbophil[5] | 45.00 | 45.00 | 45.00 | 45.00 | 45.00 | 45.00 | 0.01 | 105.00 | 45.00 | 45.00 |
| Fumed silica[6] | 5.00 | 5.00 | 5.00 | 5.00 | 5.00 | 5.00 | 5.00 | 5.00 | 5.00 | 5.00 |
| Mucosal composition[7] | 60.00 | 60.00 | 60.00 | 60.00 | 60.00 | 60.00 | 60.00 | 60.00 | 60.00 | 60.00 |

[1] Encompress ® from Edward Mendell Co. Inc., Carmel, NY, a commercially available dicalcium phosphate dihydrate.
[2] Compritol ® 885 from Gattefosse Corporation, Elmsford, NY, a commercially available glyceryl behenate.
[3] Vinol ® 125 from Air Products and Chemicals, Inc., Allentown, PA, a commercially available polyvinyl alcohol.
[4] Klucel ® HXF from Hercules, Inc., Houston, Texas, a commercially available hydroxypropyl cellulose.
[5] Carbopol ® Ex-55 Resin from B.F. Goodrich Corp., a commercially available polycarbophil.
[6] Sylloid ® 244 FP from the Davison Division of W. R. Grace and Company, a commercially available fumed silicon dioxide.
[7] Albuterol:PEG 8000 ratio of 1:2 (w/w).

An equivalent of 20 mg of albuterol in a mucosal composition of a albuterol:PEG 8000 weight in a ratio of 1:2 was included in each carrier. In vitro drug release studies as detailed in EXAMPLE 7 were performed. Plots of weight percent therapeutic agent released versus time were constructed and the drug release parame-

| Colorant[3] | — | 1.00 |
| Magnesium stearate | — | 1.00 |
| Polyvinyl alcohol[4] | 7.00 | — |
| Hydroxypropyl cellulose[5] | 0.01 | 0.75 |
| Polycarbophil[6] | 0.01 | — |

TABLE XI-continued

| | Mucoadhesive carrier composition | |
|---|---|---|
| | Weight, (mg) Per Carrier | |
| Component | Polymer matrix | Barrier film |
| Fumed silica[7] | 5.00 | — |
| PEG 8000 | 19.53 | — |
| Mucosal composition[8] | 60.00 | — |

[1] Encompress ® from Edward Mendell Co. Inc., Carmel, NY, a commercially available dicalcium phosphate dihydrate.
[2] Compritol ® 885 from Gattefossé Corporation, Elmsford, NY, a commercially available glyceryl behenate.
[3] FD & C red #40 lake from Coloron, Inc., a commercially available aluminum lake colorant.
[4] Vinol ® 125 from Air Products and Chemicals, Inc., Allentown, PA, a commercially available polyvinyl alcohol.
[5] Klucel ® HXF from Hercules, Inc., Houston, Texas, a commercially available hydroxypropyl cellulose.
[6] Carbopol ® Ex-55 Resin from B.F. Goodrich Corp., a commercially available polycarbophil.
[7] Sylloid ® 244 FP from Davison Division of W. R. Grace and Company, a commercially available fumed silicon dioxide.
[8] Piroxicam:PEG 8000 weight ratio of 1:2.

The rate of in vitro release of therapeutic agent was 5 weight percent in one hour, 9 weight percent in two hours, 13 weight percent in three hours and 24.1 weight percent in 6 hours and 56 weight percent in 23 hours. The therapeutic agent released followed an apparent zero order rate. Approximately 36–47 weight percent of the therapeutic agent remained in the carrier after 23 hours suggesting good release control by the matrix composition.

EXAMPLE 10

In vitro 17 β-estradiol release

The composition of TABLE XII, below, of a bi-laminate mucoadhesive carrier in disc form with 17 β-estradiol was prepared and tested in vitro for therapeutic agent release characteristics. The preparation and testing procedures were similar to those described in EXAMPLE 7.

TABLE XI

| | Mucoadhesive carrier composition | |
|---|---|---|
| | Weight, (mg) Per Carrier | |
| Component | Polymer matrix | Barrier film |
| Dicalcium phosphate dihydrate[1] | 27.50 | 90.50 |
| Glyceryl behenate[2] | 5.50 | 50.00 |
| Colorant[3] | — | 1.00 |
| Magnesium stearate | — | 1.00 |
| Polyvinyl alcohol[4] | 7.00 | — |
| Hydroxypropyl cellulose[5] | 45.00 | 0.75 |
| Polycarbophil[6] | 45.00 | — |
| Fumed silica[7] | 5.00 | — |
| Mucosal composition[8] | 15.00 | — |

[1] Encompress ® from Edward Mendell Co. Inc., Carmel, NY, a commercially available dicalcium phosphate dihydrate.
[2] Compritol ® 885 from Gattefossé Corporation, Elmsford, NY, a commercially available glyceryl behenate.
[3] FD & C red #40 lake from Coloron, Inc., a commercially available aluminum lake colorant.
[4] Vinol ® 125 from Air Products and Chemicals, Inc., Allentown, PA, a commercially available polyvinyl alcohol.
[5] Klucel ® HXF from Hercules, Inc., Houston, Texas, a commercially available hydroxypropyl cellulose.
[6] Carbopol ® Ex-55 Resin from B. F. Goodrich Corp., a commercially available polycarbophil.
[7] Sylloid ® 244 FP from Davison Division of W. R. Grace and Company, a commercially available fumed silicon dioxide.
[8] 17 β-estradiol:PEG 8000 weight ratio of 1:2.

The rate of in vitro release of therapeutic agent was 2.5 weight percent at 1 hour, 4 weight percent at 2 hours, 9.5 weight percent at 5 hours and 46.3 weight percent at 24 hours. The therapeutic agent release thus followed an apparent zero order process. The carrier remained intact demonstrating retention of integrity of the bi-laminate delivery system.

EXAMPLE 11

In vitro nifedipine release

The composition of TABLE XIII, below, of a mucoadhesive carrier in the form of a bi-laminate disc containing 10 mg of nifedipine was prepared. The procedures for disc preparation and in vitro release testing were similar to those of EXAMPLE 7.

TABLE XIII

| | Mucoadhesive carrier composition | |
|---|---|---|
| | Weight, (mg) Per Carrier | |
| Component | Polymer matrix | Barrier film |
| Dicalcium phosphate dihydrate[1] | 27.50 | 90.50 |
| Glyceryl behenate[2] | 5.50 | 50.00 |
| Colorant[3] | — | 1.00 |
| Magnesium stearate | — | 1.00 |
| Polyvinyl alcohol[4] | 0.01 | — |
| Hydroxypropyl cellulose[5] | 0.01 | — |
| Polycarbophil[6] | 0.01 | — |
| Fumed silica[7] | 5.00 | — |
| Mucosal composition[8] | 30.00 | — |
| PEG 8000 | 35.00 | — |

[1] Encompress ® from Edward Mendell Co. Inc., Carmel, NY a commercially available dicalcium phosphate dihydrate.
[2] Compritol ® 885 from Gattefossé Corporation, Elmsford, NY, a commercially available glyceryl behenate.
[3] FD & C red #40 lake from Coloron, Inc., a commercially available aluminum lake colorant.
[4] Vinol ® 125 from Air Products and Chemicals, Inc., Allentown, PA, a commercially available polyvinyl alcohol.
[5] Klucel ® HXF from Hercules, Inc., Houston, Texas, a commercially available hydroxypropyl cellulose.
[6] Carbopol ® Ex-55 Resin from B. F. Goodrich Corp., a commercially available polycarbophil.
[7] Sylloid ® 244 FP from Davison Division of W. R. Grace and Company, a commercially available fumed silicon dioxide.
[8] Nifedipine:PEG 8000 weight ratio of 1:2.

The rate of in vitro release of nifedipine was 4 weight percent in 1 hour, 6.5 weight percent in 2 hours, 10.7 weight percent in 4 hours, 18.7 weight percent hours and 21.0 weight percent in 8 hours suggesting a zero order therapeutic agent release from the monolithic matrix.

EXAMPLE 12

In vitro dehydroepiandrosterone release

The composition of TABLE XIV, below, of a bi-laminate mucoadhesive carrier in the form of a disc was prepared with 5 mg of dehydroepiandrosterone (DHEA), an androgen, as the therapeutic agent. The methods for preparation and in vitro release testing were similar to those described in EXAMPLE 7.

TABLE XIV

| | Mucoadhesive carrier composition | |
|---|---|---|
| | Weight, (mg) Per Carrier | |
| Component | Polymer matrix | Barrier film |
| Dicalcium phosphate dihydrate[1] | 27.50 | 90.50 |
| Glyceryl behenate[2] | 0.01 | 50.00 |
| Colorant[3] | — | 1.00 |
| Magnesium stearate | — | 1.00 |
| Polyvinyl alcohol[4] | 7.00 | — |
| Hydroxypropyl cellulose[5] | 0.01 | 0.75 |
| Polycarbophil[6] | 0.01 | — |
| Fumed silica[7] | 5.00 | — |
| Mucosal composition[8] | 15.00 | — |

TABLE XIV-continued

| | Mucoadhesive carrier composition | |
|---|---|---|
| | Weight, (mg) Per Carrier | |
| Component | Polymer matrix | Barrier film |
| PEG 8000 | 34.53 | — |

[1] Encompress ® from Edward Mendell Co. Inc., Carmel, NY a commercially available dicalcium phosphate dihydrate.
[2] Compritol ® 885 from Gattefossé Corporation, Elmsford, NY, a commercially available glyceryl behenate.
[3] FD & C red #40 lake from Coloron, Inc., a commercially available aluminum lake colorant.
[4] Vinol ® 125 from Air Products and Chemicals, Inc., Allentown, PA, a commercially available polyvinyl alcohol.
[5] Klucel ® HXF from Hercules, Inc., Houston, Texas, a commercially available hydroxypropyl cellulose.
[6] Carbopol ® Ex-55 Resin from B. F. Goodrich Corp., a commercially available polycarbophil.
[7] Sylloid ® 244 FP from Davison Division of W. R. Grace and Company, a commercially available fumed silicon dioxide.
[8] DHEA:PEG 8000 weight ratio of 1:2.

The rate of in vitro release of dehydroepiandrosterone was 20 weight percent at 6 hours, 30 weight percent at 10.5 hours, 40 weight percent at 13 hours and 50 weight percent at 23 hours. Thus controlled release of the therapeutic agent was obtained from the carrier.

EXAMPLE 13

Alternative method of applying the barrier film as a coating suspension and in vitro therapeutic agent release The components of TABLE XV, below, were used to form a bi-laminate mucoadhesive carrier.

TABLE XV

| | Mucoadhesive carrier composition | | | |
|---|---|---|---|---|
| | Polymer matrix | | Barrier film | |
| Component | Weight, (mg) | Weight % | Weight (g) | Weight % |
| Dicalcium phosphate dihydrate[1] | 85.0 | 42.5 | — | — |
| Glyceryl behenate[2] | 10.0 | 5.0 | — | — |
| Colorant[3] | — | — | 0.05 | 0.07 |
| Fumed silica[4] | 50.0 | 25.0 | — | — |
| PEG 8000 | 50.0 | 25.0 | — | — |
| Albuterol | 5.0 | 2.5 | — | — |
| Cellulose acetate-butyrate | — | — | 9.0 | 12.49 |
| Distilled acetylated monoglyceride[5] | — | — | 3.0 | 4.16 |
| Solvent solution[6] | — | — | 60.0 | 83.28 |
| Total | 200.00 | 100.00 | 72.05 | 100.00 |

[1] Encompress ® from Edward Mendell Co. Inc., Carmel, NY a commercially available dicalcium phosphate dihydrate.
[2] Compritol ® 885 from Gattefossé Corporation, Elmsford, NY, a commercially available glyceryl behenate.
[3] FD & C red #40 lake from Coloron, Inc., a commercially available aluminum lake colorant.
[4] Sylloid ® 244 FP from Davison Division of W. R. Grace and Company, a commercially available fumed silicon dioxide.
[5] Myvacet ® 945 from Eastman Chemical Products, Inc., Kingston, Tennessee, a commercially available distilled acetylated monoglyceride.
[6] Ethyl acetate:acetone in a 1:1 weight ratio evaporated during drying of the applied film.

All components for the polymer matrix equivalent to 10 carriers in disc form were screened through a 40 mesh stainless steel screen, weighed and blended. 200 Mg of this blend were compressed into approximately 13 mm×3 mm circular discs. A portion of the discs so prepared was coated manually on one side with a homogenous suspension of the compounds of the barrier film to serve as a water-insoluble barrier film. The barrier film coating suspension was prepared by dissolving the polymer and the plasticizer in the organic solvent solution followed by the addition of the FD&C Red #40 lake powder to the suspension to obtain the final suspension.

In vitro studies were conducted on these carriers to determine controlled drug release characteristics as descibed previously in EXAMPLE 7. The time to release 20%, 50%, 75% and 90% by weight of albuterol from the polymer matrix was approximately 0.8 hr, 2.6 hrs, 6 hrs, and 10.5 hrs, respectively, indicative of controlled therapeutic release from this polymer matrix comprised primarily of dry micro-particulate silicon dioxide and PEG 8000.

EXAMPLE 14

In vitro therapeutic agent release experiment of a mucoadhesive carrier having a barrier film applied as a coating suspension The components of TABLE XVI, below, were used to form a polymer matrix of a bi-laminate mucoadhesive carrier.

TABLE XVI

| | Polymer matrix composition | |
|---|---|---|
| Component | Weight, (mg) | Weight percent |
| Dicalcium phosphate dihydrate[1] | 85.0 | 42.5 |
| Glyceryl behenate[2] | 10.0 | 5.0 |
| Fumed silica[3] | 50.0 | 25.0 |
| Polyoxyalkylene block copolymer[4] | 50.0 | 25.0 |
| Albuterol | 5.0 | 2.5 |
| Total | 200.00 | 100.00 |

[1] Encompress ® from Edward Mendell Co. Inc., Carmel, NY a commercially available dicalcium phosphate dihydrate.
[2] Compritol ® 885 from Gattefossé Corporation, Elmsford, NY, a commercially available glyceryl behenate.
[3] Sylloid ® 244 FP from Davison Division of W. R. Grace and Company, a commercially available fumed silicon dioxide.
[4] Pluronic ® F-68 from BASF Wayandotte Corporation, Parsippany, New Jersey, a commercially available plyoxyalkylene block copolyer.

The procedure utilized to prepare the polymer matrix was as follows:

All components were screened through a 40 mesh stainless steel screen. An amount of each component equivalent to 10 discs was weighed. These were then mixed intimately to obtain a final blend. Polymer matrices in disc form weighing approximately 200 mg were compressed and subsequently coated with the barrier film coating suspension of EXAMPLE 13. They were dried to obtain a bi-laminate carrier in disc form containing fumed silicon dioxide as a mucoadhesive in combination with a polyoxyalkylene block copolymer, Pluronic F68, as an inert gel-forming agent.

Rate of in vitro release of therapeutic agent studies, as described in EXAMPLE 7, showed that this carrier composition released 20%, 50%, 75% and 90% by weight of albuterol at approximately 1 hr, 3.5 hrs, 8 hrs and 15 hrs, respectively. This carrier composition thus provides a controlled release matrix for therapeutic agents as exemplified by albuterol.

EXAMPLE 15

In vitro therapeutic agent release experiment of a mucoadhesive carrier having a barrier film applied as a suspension The composition of TABLE XVII, below, for a polymer matrix of a mucoadhesive carrier was prepared.

TABLE XVII

| Polymer matrix composition | | |
|---|---|---|
| Component | Weight, (mg) | Weight percent |
| Dicalcium phosphate dihydrate[1] | 37.0 | 18.5 |
| Glyceryl behenate[2] | 5.0 | 2.5 |
| Polyvinyl alcohol[3] | 10.0 | 5.0 |
| Hydroxypropyl cellulose[4] | 40.0 | 20.0 |
| Fumed silica[5] | 35.0 | 17.5 |
| Acrylic acid polymer[6] | 35.0 | 17.5 |
| PEG 3350 | 23.0 | 11.5 |
| Mucosal composition[7] | 15.0 | 7.5 |
| Total | 200.00 | 100.00 |

[1] Encompress ® from Edward Mendell Co. Inc., Carmel, NY, a commercially available dicalcium phosphate dihydrate.
[2] Compritol ® 885 from Gattefossé Corporation, Elmsford, NY, a commercially available glyceryl behenate.
[3] Vinol ® 125 from Air Products and Chemicals, Inc., Allentown, PA, a commercially available polyvinyl alcohol.
[4] Klucel ® HXF from Hercules, Inc., Houston, Texas, a commercially available hydroxypropyl cellulose.
[5] Sylloid ® 244 FP from Davison Division of W. R. Grace and Company, a commercially available fumed silicon dioxide.
[6] Carbopol ® 934P from B. F. Goodrich Corp., a commercially available acrylic acid polymer.
[7] Albuterol:PEG 8000 weight ratio of 1:2.

The method of preparation of this carrier was substantially the same as that described in EXAMPLE 6 except that the carrier included fumed silica as well. One side of the polymer matrix was coated manually with the barrier film coating suspension prepared and applied as described in EXAMPLE 13.

Rate of in vitro release of therapeutic agent studies, as disclosed in EXAMPLE 7, were performed to determine release characteristics of albuterol from this carrier. This carrier includes microfine dry silicon dioxide-polyethylene glycol in combination with Carbopol ® 934P as an hydrophilic adjuvant to provide diffusional control and possible potentiation of mucoadhesion with the silicon dioxide and PEG 3350/8000 combination. In vitro release of albuterol was 22 weight percent at 3 hours, 50 weight percent at 7.5 hours, 75 weight percent at 12 hours and 90 weight percent at 18 hours thus illustrating again a controlled release profile of this carrier.

EXAMPLE 16

In vitro therapeutic agent release experiment of a mucoadhesive carrier having a barrier film applied as a coating suspension The composition of TABLE XVIII, below, was utilized to prepare a polymer matrix of the mucoadhesive carrier.

TABLE XVIII

| Polymer matrix composition | | |
|---|---|---|
| Component | Weight, (mg) | Weight percent |
| Dicalcium phosphate dihydrate[1] | 37.0 | 18.50 |
| Glyceryl behenate[2] | 2.5 | 1.25 |
| Polyvinyl alcohol[3] | 15.0 | 7.50 |
| Hydroxypropyl cellulose[4] | 37.5 | 18.75 |
| Polycarbophil[5] | 25.0 | 12.50 |
| Fumed silica[6] | 35.0 | 17.50 |
| PEG 3350 | 33.0 | 16.50 |
| Mucosal composition[7] | 15.0 | 7.50 |
| Total | 200.00 | 100.00 |

[1] Encompress ® from Edward Mendell Co. Inc., Carmel, NY, a commercially available dicalcium phosphate dihydrate.
[2] Compritol ® 885 from Gattefossé Corporation, Elmsford, NY, a commercially available glyceryl behenate.
[3] Vinol ® 125 from Air Products and Chemicals, Inc., Allentown, PA, a commercially available polyvinyl alcohol.
[4] Klucel ® HXF from Hercules, Inc., Houston, Texas, a commercially available hydroxypropyl cellulose.
[5] Carbopol ® Ex-55 Resin from B. F. Goodrich Corp., a commercially available polycarbophil.
[6] Sylloid ® 244 FP from Davison Division of W. R. Grace and Company, a commercially available fumed silicon dioxide.
[7] Albuterol:PEG 8000 weight ratio of 1:2.

The procedure to prepare the polymer matrix of the carrier was similar to that described in EXAMPLE 7. A water-insoluble barrier film as illustrated in EXAMPLE 13 was applied manually and air dried to remove solvents.

A rate of in vitro release of therapeutic agent study of this carrier was performed according to the procedure disclosed in EXAMPLE 7. In vitro release of albuterol was 27 weight percent at 2 hours, 50 weight percent at 5 hours, 73 weight percent at 10 hours and 90 weight percent at 19 hours thus demonstrating the controlled release property of the carrier.

EXAMPLE 17

In vitro therapeutic agent release experiment of a mucoadhesive carrier having a barrier film applied as a coating suspension The composition of TABLE XIX, below, was utilized to prepare a mucoadhesive sugar alcohol carrier matrix having 17 β-estradiol (micronized) distributed therein.

TABLE XIX

| Carrier matrix composition | | |
|---|---|---|
| Component | Weight, (mg) | Weight percent |
| Dicalcium phosphate dihydrate[1] | 65.0 | 32.5 |
| Glyceryl behenate[2] | 10.0 | 5.0 |
| Fumed silica[3] | 50.0 | 25.0 |
| Mannitol | 50.0 | 25.0 |
| 17 β-estradiol | 5.0 | 2.5 |
| Lactose | 20.0 | 10.0 |
| Total | 200.00 | 100.00 |

[1] Encompress ® from Edward Mendell Co. Inc., Carmel, NY, a commercially available dicalcium phosphate dihydrate, a particulate controlled release modulating agent.
[2] Compritol ® 885 from Gattefossé Corporation, Elmsford, NY, a commercially available glyceryl behenate, a lubricant.
[3] Sylloid ® 244 FP from Davison Division of W. R. Grace and Company, a commercially available fumed silicon dioxide.

All components of the matrix were sieved through a 60 mesh stainless steel screen. All components equivalent to 10 matrices were weighed, blended and compressed into 10 matrix discs. One side of the matrix disc was film-coated manually with the barrier film coating suspension as disclosed in EXAMPLE 13. The film coated side was air dried and the resulting mucoadhesive carrier discs were then tested for release of estradiol by the same test procedure as described in EXAMPLE 7.

The rate of in vitro release of 17 β-estradiol was 9.5 weight percent at 5 hours, 15 weight percent at 10 hours, 17 weight percent at 15 hours and 19.5 weight percent at 20 hours thus demonstrating controlled release property of the carrier.

The foregoing Example also illustrates that a mucoadhesive matrix can be prepared utilizing a sugar alcohol, such as mannitol, in combination with fumed silica. Other sugar alcohols suitable for this purpose are inositol, xylitol, sorbitol, and the like. A lubricant such as glyceryl behenate is included in the matrix composition to facilitate manufacture by direct compression techniques. An absorbent filler such as dicalcium phosphate dihydrate was incorporated into the matrix composition to modulate the medicament release rate.

EXAMPLE 18

Mucoadhesive breath fresheners

Several mucoadhesive carriers containing flavoring in the barrier film were prepared as mucoadhesive controlled release breath fresheners or deodorants. These compositions are illustrated in TABLE XX hereinbelow. The composition of the polymer matrix was held constant. The flavoring of the composition of the barrier film was varied to obtain Bi, Bii and Biii. The flavorings utilized were peppermint oil USP, cinnamicaldehyde FCC and spearmint oil NF.

Physical mixtures of the individual flavorings and polyethylene glycol (PEG) 8000 were prepared by the same procedure described in EXAMPLE 6. Then, components were processed in a manner similar to EXAMPLE 7 to obtain carriers.

TABLE XX

Mucoadhesive breath freshener carriers

| Component | Polymer matrix weight (mg) | Barrier films, weight (mg) Bi | Bii | Bii |
|---|---|---|---|---|
| Dicalcium phosphate dihydrate[1] | 30.0 | 45.0 | 45.0 | 45.0 |
| Glyceryl behenate[2] | 7.5 | 45.0 | 45.0 | 45.0 |
| Colorant[3] | — | 1.0 | 1.0 | 1.0 |
| Magnesium stearate | — | 1.0 | 1.0 | 1.0 |
| Polyvinyl alcohol[4] | 7.5 | — | — | — |
| Hydroxypropyl cellulose[5] | 30.0 | — | — | — |
| Fumed silica[6] | 37.5 | — | — | — |
| PEG 8000 | 37.5 | 43.0 | 43.0 | 43.0 |
| Peppermint Oil USP | — | 15.0 | — | — |
| Cinnamicaldehyde FCC | — | — | 15.0 | — |
| Spearmint Oil NF | — | — | — | 15.0 |

[1]Encompress ® from Edward Mendell Co. Inc., Carmel, NY, a commercially available dicalcium phosphate dihydrate.
[2]Compritol ® 885 from Gattefossé Corporation, Elmsford, NY, a commercially available glyceryl behenate.
[3]FD & C red #40 lake from Coloron, Inc., a commercially available aluminum lake colorant.
[4]Vinol ® 125 from Air Products and Chemicals Inc., Allentown, PA, a commercially available polyvinyl alcohol.
[5]Klucel ® HXF from Hercules, Inc., Houston, Texas, a commercially available hydroxypropyl cellulose.
[6]Sylloid ® 244 FP from Davison Division of W. R. Grace and Company, a commercially available fumed silicon dioxide.

EXAMPLE 19

Evaluation of the mucoadhesive properties of mucoadhesive carriers

The adhesiveness of mucoadhesive carriers prepared with silicon dioxide, polyethylene glycol and other polymeric components was performed with compositions illustrated in EXAMPLE 13, EXAMPLE 14 and EXAMPLE 15.

Male albino rabbits were sacrificed and the stomachs were removed and placed in ice cold aerated normal saline. The tissue was rinsed well to remove any partially digested food while still maintaining mucous integrity. A piece of tissue was cut, draped over a weighted support, firmly attached, and placed in room temperature normal saline. Another piece of tissue, with muscle removed, was mounted onto a rubber stopper. A sample of mucoadhesive carrier was placed on top of the mucin surface of the tissue on the stopper and evenly distributed. The stopper was then placed on a tensiometer and zeroed with a counter weight. Using a lab jack, the tissue on the weighted support was allowed to come into contact with the tissue on the stopper. The full weight of the stopper was allowed to rest on the weighted support and kept there for 60 seconds. The interaction of the two membranes was then measured by increasing the counter weight until a separation of the interface was observed. Measurements were in milligrams. (Note: The maximum weight was 6500 mg. Any adhesion above this point could not be measured accurately.)

The adhesive properties of the three carriers supplied were too strong for the tensiometer to measure in air without buffer which is suggestive of excellent adhesion of the discs to the mucus in vitro.

EXAMPLE 20

Mucoadhesive carrier containing a vitamin

The composition of TABLE XXI, below, was utilized to prepare a polymer matrix of a mucoadhesive carrier of a vitamin $B_{12}$, for trans-mucosal absorption of the vitamin.

TABLE XXI

Mucoadhesive vitamin carrier

| Component | Polymer matrix, weight (mg) |
|---|---|
| Dicalcium phosphate dihydrate[1] | 85.0 |
| Glyceryl behenate[2] | 10.0 |
| Fumed silica[3] | 50.0 |
| PEG 8000 | 45.0 |
| Vitamin $B_{12}$ | 10.0 |

[1]Encompress ® from Edward Mendell Co. Inc., Carmel, NY, a commercially available dicalcium phosphate dihydrate.
[2]Compritol ® 885 from Gattefossé Corporation, Elmsford, NY, a commercially available glyceryl behenate.
[3]Sylloid ® 244 FP from Davison Division of W. R. Grace and Company, a commercially available fumed silicon dioxide.

All components were sieved through a 60 mesh stainless steel screen. Components equivalent to ten polymer matrices were weighed, blended together and compressed into ten polymer matrix discs. The polymer matrix discs were then coated on a side with a barrier film coating suspension. The composition and procedure for application of this suspension are described in EXAMPLE 13.

This invention has been described in terms of specific embodiments set forth in detail, but it should be understood that these are by way of illustration only and that the invention is not necessarily limited thereto. Modifications and variations will be apparent from this disclosure, drawings and appended claims, and may be resorted to without departing from the skill of this invention, as those skilled in the art will readily understand. Accordingly, such variations and modifications of the disclosed product are considered to be within the purview and scope of this invention and the following claims.

We claim:

1. A therapeutic dosage form comprising an anhydrous but hydratable monolithic polymer matrix that contains amorphous fumed silica as well as a therapeutic agent and defines a mucoadhesive face, and a water-insoluble barrier layer secured to said polymer matrix and defining a non-adhesive face; said therapeutic agent being dehydroepiandrosterone, said polymer being polyethylene glycol having a number average molecular weight of about 4,000, and the weight ratio of dehydroepiandrosterone to said polyethylene glycol being about 1:4, respectively.

2. A therapeutic dosage form comprising an anhydrous but hydratable monolithic polymer matrix that contains amorphous fumed silica as well as a therapeutic agent and defines a mucoadhesive face, and a water-insoluble barrier layer secured to said polymer matrix and defining a non-adhesive face; said therapeutic agent being nifedipine, said polymer being polyethylene glycol having a number average molecular weight of about 8,000, and the weight ratio of nifedipine to said polyethylene glycol being about 1:2, respectively.

3. A therapeutic dosage form comprising an anhydrous but hydratable monolithic polymer matrix that contains amorphous fumed silica as well as a therapeutic agent and defines a mucoadhesive face, and a water-insoluble barrier layer secured to said polymer matrix and defining a non-adhesive face; said therapeutic agent being piroxicam, said polymer being polyethylene glycol having a number average molecular weight of about 8,000, and the weight ratio of piroxicam to said polyethylene glycol being about 1:2, respectively.

4. A therapeutic dosage form comprising an anhydrous but hydratable monolithic polymer matrix that contains amorphous fumed silica as well as a therapeutic agent and defines a mucoadhesive face, and a water-insoluble barrier layer secured to said polymer matrix and defining a non-adhesive face; said therapeutic agent being albuterol, said polymer being polyethylene glycol having a number average molecular weight of about 8,000, and the weight ratio of albuterol to said polyethylene glycol being about 1:2, respectively.

5. A therapeutic dosage form comprising an anhydrous but hydratable monolithic polymer matrix that contains amorphous fumed silica as well as a therapeutic agent and defines a mucoadhesive face, and a water-insoluble barrier layer secured to said polymer matrix and defining a non-adhesive face; said therapeutic agent being dehydroepiandrosterone, said polymer being polyethylene glycol having a number average molecular weight of about 8,000, and the weight ratio of dehydroepiandrosterone to said polyethylene glycol being about 1:2, respectively.

6. A therapeutic dosage form comprising an anhydrous but hydratable monolithic polymer matrix that contains amorphous fumed silica as well as a therapeutic agent and defines a mucoadhesive face, and a water-insoluble barrier layer secured to said polymer matrix and defining a non-adhesive face; said therapeutic agent being phenylpropanolamine, said polymer being polyethylene glycol having a number average molecular weight of about 8,000, and the weight ratio of phenylpropanolamine to said polyethylene glycol being about 1:2, respectively.

7. A therapeutic dosage form comprising an anhydrous but hydratable monolithic polymer matrix that contains amorphous fumed silica as well as a therapeutic agent and defines a mucoadhesive face, and a water-insoluble barrier layer secured to said polymer matrix and defining a non-adhesive face; said therapeutic agent being 17 $\beta$-estradiol, said polymer being polyethylene glycol having a number average molecular weight of about 8,000, and the weight ratio of 17 $\beta$-estradiol to said polyethylene glycol being about 1:2, respectively.

8. The therapeutic dosage form in accordance with claims 1, 2, 3, 4, 5, 6, or 7 and provided with a retrieving element embedded in said polymer matrix.

9. The therapeutic dosage form in accordance with claim 8 wherein the retrieving element is a string segment.

10. The therapeutic dosage form in accordance with claim 8 wherein the retrieving element is a planar member.

11. The therapeutic dosage form in accordance with claim 10 wherein said planar member is perforated.

* * * * *